(12) United States Patent
Rosenstiel

(10) Patent No.: US 6,607,756 B1
(45) Date of Patent: Aug. 19, 2003

(54) METHOD AND TOPICAL COMPOUND FOR TREATMENT OF EDEMA

(76) Inventor: Leonie Rosenstiel, 7542 Bear Canyon Rd., NE., Albuquerque, NM (US) 87109

( * ) Notice: Subject to any disclaimer, the term of this patent is extended or adjusted under 35 U.S.C. 154(b) by 0 days.

(21) Appl. No.: 09/785,576

(22) Filed: Feb. 15, 2001

Related U.S. Application Data

(63) Continuation-in-part of application No. 09/398,334, filed on Sep. 17, 1999, now abandoned.
(60) Provisional application No. 60/107,605, filed on Nov. 9, 1998.

(51) Int. Cl.$^7$ .................................................. A61K 35/78
(52) U.S. Cl. ...................... 424/748; 424/725; 424/739; 424/756
(58) Field of Search ................... 424/748, 739, 424/756, 725

(56) References Cited

U.S. PATENT DOCUMENTS

| | | |
|---|---|---|
| 3,988,437 A | 10/1976 | Bradner |
| 4,663,315 A | 5/1987 | Hasegawa et al. |
| 6,269,817 B1 * | 8/2001 | Nagshima et al. |

FOREIGN PATENT DOCUMENTS

| | | | |
|---|---|---|---|
| CA | 2097337 | * | 5/1995 |
| CH | 688787 A5 | * | 3/1998 |

OTHER PUBLICATIONS

CAPLUS abstract of ES 2081771 A1 (1996).*
Derwent abstract of CN 1104113 A (1995).*
Derwent abstract of CN 1134819 (1996).*

* cited by examiner

Primary Examiner—Leon B. Lankford, Jr.
Assistant Examiner—Susan D Coe
(74) Attorney, Agent, or Firm—Stephen A. Slusher

(57) ABSTRACT

A herbal composition that aids in the relief of symptoms caused by edema, cyanosis, blood stasis, neuropathy and related conditions is provided, including one or more of cayenne extract, myrrh essential oil, frankincense essential oil, cinnamon essential oil, ginger essential oil, and powdered saffron in a carrier oil, preferably safflower oil. Further provided is a method of administration of the herbal composition, by application to the exterior surfaces of the human body using massage strokes in the direction of venous blood flow.

27 Claims, No Drawings

METHOD AND TOPICAL COMPOUND FOR TREATMENT OF EDEMA

CROSS-REFERENCE TO RELATED APPLICATIONS

This application is a continuation-in-part application of U.S. patent application Ser. No. 09/398,334, entitled "Topical Compound for Relief of Symptoms Associated with Diminished Blood Flow", by Leonie Rosenstiel-Orrmont, filed on Sep. 17, 1999 now abandoned, which application claims the benefit of the filing of U.S. Provisional Patent Application Serial No. 60/107,605, entitled "Dayspring Oil #1: Transcutaneous Treatment for Symptoms of Diminished Organic, Glandular, Veinous or Arterial Blood Volume", filed on Nov. 9, 1998, and the specification of each of the foregoing is incorporated herein by reference.

BACKGROUND OF THE INVENTION

1. Field of the Invention (Technical Field)

The present invention is directed to an herbal compound and method of administration. More particularly, the present invention is directed to an herbal compound and method of administration that aids in the relief of symptoms caused by edema, cyanosis, blood stasis, and neuropathy.

2. Background Art

Many people, especially elderly people, suffer from medical conditions that limit or decrease the blood flow throughout their bodies. These conditions can result in various medical states such as edema (an accumulation of an excessive amount of watery fluids in cells, tissues, or serous cavities), cyanosis (blue or purple coloration of the skin and mucous membrane due to deficient oxygenation of the blood), blood stasis (pooling of blood due to lack of blood flow), neuropathy, and other similar medical conditions.

These medical conditions can frequently be treated by conventional medical procedures and drugs. However, many people find the medical procedures to be invasive and suffer undesirable side effects from the drugs. Others find that the medical procedures and drugs do not cure, or even alleviate, their conditions. These people seek alternatives to conventional modem medicine for their treatment.

Often treatment for the conditions mentioned above involves various forms of massage therapy. This therapy is designed to increase blood flow throughout the body, and sometimes specifically to aid in the drainage of lymph fluid and other edematous accumulations. To assist with massage therapy, therapists typically use a variety of ointments, lotions, and oils. These lotions and oils can differ greatly in their therapeutic value. For patients suffering from edema and the like, an oil which assists their therapist by increasing blood flow would become a valuable tool in conquering or at least alleviating their symptoms. Additionally, individuals can treat themselves with various forms of massage therapy.

SUMMARY OF THE INVENTION (DISCLOSURE OF THE INVENTION)

A new herbal composition and method of administration that aids in the relief of symptoms caused by edema, cyanosis, blood stasis, and neuropathy is disclosed. The herbal composition of the present invention includes cayenne extract, myrrh essential oil, frankincense essential oil, cinnamon essential oil, ginger essential oil, powdered saffron and a carrier oil. This carrier oil is preferably safflower oil. In a preferred embodiment, the herbal composition is a liquid which is applied to the exterior surfaces of the human body. On the limbs, the herbal composition is applied with massage strokes in the direction of heart, while on the trunk, the herbal composition may be applied with widening spiral massage strokes over the area to be treated.

A primary object of the present invention is to provide a composition and method for the treatment of edema, cyanosis and other conditions associated with diminished blood flow.

Another object of the present invention is to provide a method of administration of an oil-based herbal composition for treatment of edema, cyanosis and other conditions associated with diminished blood flow, in which method the oil based herbal composition is applied to extremities by massage strokes, with the strokes in the direction of the heart, with the venous flow, and is applied to the trunk and other body parts in widening spiral massage strokes, centered on the area to be treated.

Another object of the present invention is to provide a herbal composition which has safflower oil as the oil-based carrier, and includes one or more of cayenne extract, myrrh essential oil, frankincense essential oil, cinnamon essential oil, ginger essential oil, and powdered saffron.

A primary advantage of the present invention is that it provides relief from edema, varicose veins, cyanosis, and other conditions and symptoms associated with poor circulation or diminished blood flow by means of an externally-applied, oil-based herbal composition. Because the compound is not ingested, it need not undergo metabolism by the liver. As a result, the dangers posed by interaction with oral medications the patient may be taking are greatly decreased or eliminated.

Other objects, advantages and novel features, and further scope of applicability of the present invention will be set forth in part in the detailed description to follow, and in part will become apparent to those skilled in the art upon examination of the following, or may be learned by practice of the invention. The objects and advantages of the invention may be realized and attained by means of the instrumentalities and combinations particularly pointed out in the appended claims.

DESCRIPTION OF THE PREFERRED EMBODIMENTS

(BEST MODES FOR CARRYING OUT THE INVENTION)

While the making and using of the various embodiments of the present invention are discussed in detail below, it should be appreciated that the present invention provides many applicable inventive concepts that can be embodied in a wider variety of specific contexts. Specific embodiments discussed herein are merely illustrative of specific ways to make and use the invention and do not limit the scope of the invention.

The present invention is directed to an herbal composition and method of application that aids in the relief of symptoms caused by edema, cyanosis, blood stasis, neuropathy and related or similar conditions. In a preferred embodiment of the invention, the herbal composition includes cayenne extract (capsicum), myrrh, frankincense, cinnamon, ginger, saffron and a carrier oil. The myrrh, frankincense, cinnamon, and ginger are in their essential oil forms. The saffron is in a finely powdered form. The carrier oil is preferably safflower oil, although other similar oils may be used.

Cayenne extract, also known as capsicum (Capsicum spp.) part of the Solanaceae family, is alterative, stimulating and a tonic. In a preferred embodiment of the invention, an extract that is 95 percent grain alcohol is used. Cayenne stimulates blood flow. Cayenne is also reported to increase the power of other herbs by acting as a catalyst therefor, and thereby acting to increase their effectiveness. Cayenne is high in vitamin A, B-complex, C, iron and calcium. In the present invention, cayenne serves to increase blood flow and alleviate pain. By this action, it helps to drain pooled blood, eliminating blood stasis and stimulating lymph drainage while it decreases associated pain. When the compound is applied topically, the cayenne acts in these capacities.

Myrrh (Commiphora myrrha) is an aromatic resin that has been considered an important healing agent, having been used for many years as an astringent for sore gums and gingivitis, a stimulant, and an antispasmodic. In the present invention, myrrh is used in its essential oil form. The myrrh is used for its circulatory stimulating powers in the present invention Frankincense (Olibanum) is an aromatic that has been considered an important agent in the treatment of various forms of pain. Frankincense has a pungent-warm stimulant effect when applied to the body thus making it effective in the treatment of diminished blood flow to which the present invention is directed.

Cinnamon (Cortex Cinnamoni Cassiae) is an aromatic, astringent, and stimulant. In its essential oil form, as used in the present invention, cinnamon is also a septic, antifungal, antiviral, bactericidal, and larvicidal. Cinnamon is high in potassium and vitamin A. The essential oils of cinnamon can be made from the leaves, bark, stems, or roots. In a preferred embodiment of the invention, the essential oil is made from the best quality cinnamon bark, which is commonly thick. In the present invention, cinnamon bark oil is used because of its natural assistance with cardiovascular and circulatory blood flow.

Ginger (Zingiber officinale, part of the Zingiberaceae family) is antispasmodic, diaphoretic, rubefacient, and stimulant. In a preferred embodiment, the essential oil is used. In the present invention, ginger is used for its stimulating properties. In particular, the ginger is used to assist in stimulating arterial circulation and for its warming properties as well as to diminish general pains and aches, and to stimulate peripheral circulation. Ginger also has anti-oxidant and anti-microbial effects and contains vitamins A, B-complex and C.

Saffron (Crocus Sativus, Stigma Croci) is a sedative, stimulant, antispasmodic, and diaphoretic. It has also been used as a pain reliever and dry skin balm. In the present invention, pure powdered saffron is used. The saffron should be ground sufficiently fine to appear to dissolve or be suspended in the liquid compound. As used in the present invention, saffron functions to increase blood flow, to relieve pain and to prevent the other herbs from unduly drying the patient's skin.

In the present invention, a preferred carrier oil is safflower oil. Safflower oil lowers cholesterol and triglycerides when taken internally. It is being used in the composition for its use as a dispersing agent for accumulated blood and/or fluids. By using safflower oil, the strengths and actions of the other oils are enhanced.

In a preferred embodiment, the herbs are grown naturally, by means of organic farming and harvesting methods, so that contamination from pesticides, chemical fertilizers and the like is minimized. For the myrrh, frankincense, cinnamon, and ginger, it is preferred to use 100 percent essential oil. The cayenne extract should comprise between about 7 to 10 percent of the herbal composition. The myrrh and frankincense should comprise between about 5 to 7 percent each of the herbal composition. The cinnamon should comprise between about 3 to 5 percent of the herbal composition, The ginger should be at least 3 percent of the herbal composition. The saffron should be at least 0.015 grams. The carrier should comprise between about 68 to 75 percent of the herbal composition.

In using the herbal composition of the present invention, the mode of administration is of critical importance. Swedish massage is contraindicated for patients with various types of circulatory disorders, many of whom suffer from the symptoms outlined above. It is axiomatic, therefore, that they cannot receive Swedish massage. Such patients often, however, receive lymphatic massage specifically to treat such conditions as edema. In lymphatic massage, strokes are always done away from the heart, in the direction of arterial blood flow. Thus, for example, a typical massage stroke for such patients may commence on the thigh and terminate below the knee, or commence on the upper arm and terminate below the elbow or even at the wrist. In the use of the herbal composition of the present invention, it has surprisingly and unexpectedly been discovered that its use with massage strokes towards the heart, in the direction of the venous blood flow, provides markedly superior results, and that, conversely, its use with conventional massage techniques may actually exacerbate the patient's condition.

When used on an extremity, the herbal composition of the present invention is applied with long, firm massage strokes in the direction of the heart, or with the venous blood flow. For application to joints, such as the wrist or ankle, the herbal composition may be applied around the joint and then up the extremity in the direction of the heart. For application to the trunk, the application may be in a widening spiral over the affected part. These massage techniques are intended, in part, to increase the spreading and dispersing action of the ingredients in the herbal composition.

The frequency of administration is also a significant factor in the effectiveness of the treatment. Cyclic or periodic administration is preferred over continuous use, both because of the potential for adverse reaction to one or more ingredients, and to decrease or inhibit development of resistance or tolerance to the herbal composition of this invention.

In a preferred embodiment, the herbal composition of the present invention is applied utilizing the described massage techniques for a period of between six and ten days, with application twice each day. Thereafter, the preparation is not used for a period of one or more days, after which another cycle of application of the oil may be employed as appropriate.

The herbal composition of the present invention may be made using the ingredients and quantities set forth in TABLE 1:

TABLE 1

| Herbal or Oil Constituent | Volume or Weight |
| --- | --- |
| Cayenne extract | 40–60 milliliters |
| Myrrh | 30–40 milliliters |
| Frankincense | 30–40 milliliters |
| Cinnamon | 20–30 milliliters |
| Ginger | 15–30 milliliters |
| Saffron | .015–.03 grams |
| Safflower Oil | 285–590 milliliters |

INDUSTRIAL APPLICABILITY

The invention is further illustrated by the following non-limiting examples.

EXAMPLE 1

A preparation was made using the ingredients and quantities specified in TABLE 2:

TABLE 2

| Herbal or Oil Constituent | Volume or Weight |
| --- | --- |
| Cayenne extract (in 95% grain alcohol) | 60 milliliters |
| Myrrh (essential oil) | 40 milliliters |
| Frankincense (essential oil) | 40 milliliters |
| Cinnamon (essential oil from bark) | 30 milliliters |
| Ginger (essential oil) | 30 milliliters |
| Saffron (pure powdered) | .03 grams |
| Safflower Oil (pure pressed) | 590 milliliters |

The resulting oil-based herbal composition was mixed by shaking, and stored in a dark-colored glass bottle, out of direct sunlight, and preferably in a cool and dark environment. Prior to use, the oil was shaken. Subsequent to initial opening, the resulting oil-based herbal composition did not need refrigeration if used within 2 months.

A weaker version was also made, composed of 40 mL cayenne extract, 30 mL myrrh, 30 mL frankincense, 20 mL cinnamon, 15 mL ginger, 0.015 g saffron in a base of 285 mL safflower oil (the "weaker version") which was used initially with certain patients.

EXAMPLE 2

An 87-year old female was seen who had developed a feeling of "heaviness" in the legs for several days, followed that morning by severe pitting edema, approximately as 2+by standard medical terminology, along with cyanosis of both feet and ankles. These symptoms were new, although the patient described her legs as feeling perpetually cold, even in 85–90 degree weather. The oil-based herbal composition of Example 1 was administered by long massage strokes in the direction of the heart over the affected areas, consisting of the lower legs and ankles. The day following administration, the patient reported that she lost almost three pounds of water weight overnight, and her legs were almost normal in appearance. A weaker version (i.e., 40 mL cayenne extract, 30 mL myrrh, 30 mL frankincense, 20 mL cinnamon, 15 mL ginger, 0.015 g saffron in a base of 285 mL safflower oil) of oil-based herbal composition of Example 1 was administered on a daily basis, with massage strokes in the direction of the heart. Within a week, the patient's legs had returned to full sensation and the patient reported that her legs no longer felt heavy. It was then felt prudent to attempt to increase the dosage, since the patient had shown no intolerance or allergic reaction to the initial compound. By the end of the second cycle of administration, after the composition had been changed to the full-strength dosage shown in Table 1 (i.e., 60 mL cayenne extract, 40 mL myrrh, 40 mL frankincense, 30 mL cinnamon, 30 mL ginger, 0.03 g saffron in a base of 590 mL safflower oil) there was no visible edema and her varicose and spider veins had diminished greatly in size and started to fade. All traces of cyanosis had gone and the legs were of normal temperature. The patient continued to use the oil in cycles for 2½ years. At the 2½ year point, one varicose vein the patient reported having had for over 50 years is no longer visible, along with approximately ⅔ of visible spider veins. No other medical treatments had been used to aid with circulation; nor had any standard medical treatments for varicose veins ever been used by this patient. Due to the method of administration of the oil of Example 1, she has neither become sensitized to the oil, such as by developing skin irritation at the site of the application, nor has she developed a need for larger dosages.

During the initial weeks of treatment using the described protocol, one health aide applied the oil-based herbal composition of Example 1 by massaging down the patient's legs, or away from the heart and in the direction of arterial blood flow, according to standard massage directions for patients with edema. The day following this application, the amount of visible edema had substantially increased. Subsequent application of the oil-based herbal composition of Example 1 in the correct manner, by massage strokes in the direction of the heart, eliminated this problem within several days of administration.

EXAMPLE 3

A female patient, aged about 60, obtained relief from diabetic neuropathy of the arms and hands following administration of the full-strength oil-based herbal composition of Example 1 and method of administration of Example 2. Briefly, the oil-based herbal composition of Example 1 was applied by massage strokes in the direction of the heart, commencing at the hands and going up the arm. After one week of application, the patient reported she felt "tingling" where before she had had no sensation at all. Normal feeling returned to the limbs and hands within one month of commencing treatment using the full-strength oil-based herbal composition of Example 1. This patient also reported that her blood pressure was normalized and blood sugar lowered from 120 to 90. The patient was taking Coumadin, a prescription drug to inhibit clotting, and experienced no negative interactions.

EXAMPLE 4

A female patient, about 50 years of age, was seen who had had multiple sclerosis for twenty years. On arrival at the doctor's office the patient was unable to stand or walk without assistance and found it difficult to get up on treatment table due to painful limbs. After application of the full-strength dosage of the oil-based herbal composition of Example 1 using the method of administration, on all four limbs, of Example 2, the patient was able to get off table unaided and to walk out unassisted.

EXAMPLE 5

A male patient, age 61, was seen with longstanding (over 20 years) diminished circulation, dry skin and diminished sensation, along with a feeling of "heaviness" and constant dull pain in the lower extremities. Application of the weaker version of the oil-based herbal composition of Example 1 using the method of Example 2 reduced all symptoms after the first application. The patient reported that he felt comfortable in the lower extremities for the first time in years. The process was hastened and the results greatly increased when the dosage was changed to the full-strength dosage of Example 1.

EXAMPLE 6

A male patient, age 78, was seen with complaints of fifteen years of weakness in the legs leading to problems with balance, along with dry skin and diminished sensation in the lower extremities. Lower limbs were cool to the touch.

The full-strength oil-based herbal composition of Example 1 was applied to the lower extremities using the method of Example 2, with massage strokes toward the heart, on a daily basis. Within one week of application, the patient reported sensation increased to the affected areas. By the third week, the visible dry skin was beginning to heal. The patient discontinued application because he did not like the massage process; within one month the patient reported that his symptoms had all returned.

EXAMPLE 7

A female patient, in her 20's, was seen with swelling due to sub-acute tendonitis. One application of the full-strength oil-based herbal composition of Example 1 using the methods of Example 2 reduced visible swelling and eliminated reports of pain.

EXAMPLE 8

A female patient, age 65, was seen with severe pitting lymphedema and agonizing pain in one leg due to sequelae of cancer treatment, including radiation, chemotherapy and surgery during which lymph glands in the groin had been removed. The patient had been advised to have her leg amputated because her doctors were unable to offer anything other than narcotics for pain relief, and the patient did not want to take these drugs. After the first application of the full-strength oil-based herbal composition of Example 1, the patient felt considerably improved. The patient did not take the oil with her; it was not applied again until the next office visit. Due to the fact that the therapist had neglected to give her the bottle to take with her for self-administration between office visits, although the edema was much reduced on the second day, it began to return during the week. The patient reported that the edema worsened during the intervening week, but only when she stood for long periods. However, it never was as serious as when the patient first presented. Administration of the full-strength oil-based herbal composition of Example 1 using the methods of Example 2 the second week removed the edema; pain diminished after the second administration to the point where patient was able to stand and walk.

EXAMPLE 9

A female patient, age 53, was seen who reported a "heavy" feeling in legs, accompanied with extensive spider veins and painful varicosities, numbness and pain in legs. Pain, which had been almost constant since 1985, was gone in one week following administration of the stronger oil-based herbal composition of Example 1 using the methods of Example 2. Spider veins began to fade during the first two administrations of the oil-based herbal composition of Example 1. The patient has used the full-strength oil-based herbal composition in Example 1 irregularly (regularly, in cycles of 6 days on, 1 day off, for a month, then off for 4 or 5 months) for approximately two years. The patient has reported leg pain only three times during that period, for a period of hours each time. Numbness is gone; varicosities have diminished by about ⅓, as have spider veins. The patient also reports that the "heavy" feeling in the legs is gone. There has been no evidence of sensitization or allergic reaction to the preparation.

EXAMPLE 10

A female patient, age 89, was seen with a suspected MI (myocardial infarction) in progress. The patient refused the health aide's offer to call emergency ambulance service. Pulse was irregularly irregular, breathing rapid and shallow. Patient complained of strong pressure on the chest along with nausea, but without vomiting, following an unusually heavy meal. The pain was reported to have lasted 30 minutes. The full-strength oil-based herbal composition of Example 1 was massaged in circular strokes over the chest (cardiac area). The patient reported that the pain subsided within two minutes of administration, and an electrocardiogram taken the following day at the emergency room showed no major cardiac or circulatory abnormalities.

The preceding examples can be repeated with similar success by substituting the generically or specifically described reactants and/or operating conditions of this invention for those used in the preceding examples.

Although the invention has been described in detail with particular reference to these preferred embodiments, other embodiments can achieve the same results. Variations and modifications of the present invention will be obvious to those skilled in the art and it is intended to cover in the appended claims all such modifications and equivalents. The entire disclosures of all references, applications, patents, and publications cited above are hereby incorporated by reference.

What is claimed is:

1. A method of treating an area of diminished lymph flow in a patient, comprising the steps of:
   preparing an herbal composition comprising ginger, myrrh and frankincense in a carrier oil;
   applying the herbal composition by topical administration to the skin about the area of diminished lymph flow with massage strokes in the direction of venous blood flow.

2. The method claim 1, further comprising applying such herbal application on at least a daily basis for a period of at least six days and no more than ten days.

3. The method of claim 1, wherein the carrier oil is safflower oil.

4. The method of claim 3, wherein each of the ginger, myrrh and frankincense is in the form of a substantially pure essential oil.

5. The method of claim 4, wherein herbal composition comprises a formulation containing relative amounts of between about 15 and 30 mL of essential oil of ginger, between about 30 and 40 mL of essential oil of myrrh, between about 30 and 40 mL of essential oil of frankincense and between about 285 and 590 mL of safflower oil.

6. The method of claim 5, wherein the herbal composition further comprises between about 40 and 60 mL of an extract of cayenne.

7. The method of claim 6, wherein the extract of cayenne comprises at least 95 percent grain alcohol.

8. The method of claim 5, wherein the herbal composition further comprises cinnamon.

9. The method of claim 8, wherein the cinnamon comprises between about 20 and 30 mL of an essential oil of cinnamon bark.

10. The method of claim 5, wherein the herbal composition further comprises saffron.

11. The method of claim 10, wherein the saffron comprises between about 0.015 and 0.03 grams of powdered saffron.

12. The method of claim 1, wherein the area of diminished lymph flow comprises at least a part of a limb of the patient, and the massage strokes in the direction of venous blood flow are along said limb, in the direction of the heart.

13. The method of claim 1, wherein the area of diminished lymph flow comprises at least a part of the trunk of the patient, and the massage strokes in the direction of venous blood flow are in a widening spiral centered over the area of diminished nerve function, lymph flow or blood flow.

14. The method of claim 1 wherein the area of diminished lymph flow results from edema.

15. A method of treating an area of edema in a patient, comprising the steps of:

preparing an herbal composition comprising ginger, myrrh and frankincense in a carrier oil;

applying the herbal composition by topical administration to the skin about the area of edema with massage strokes in the direction of venous blood flow.

16. The method claim 15, further comprising applying such herbal application on at least a daily basis for a period of at least six days and no more than ten days.

17. The method or claim 15, wherein the carrier oil is safflower oil.

18. The method of claim 17, wherein each of the ginger, myrrh and frankincense is in the form of a substantially pure essential oil.

19. The method of claim 18, wherein herbal composition comprises a formulation containing relative amounts of between about 15 and 30 mL of essential oil of ginger, between about 30 and 40 mL of essential oil of myrrh, between about 30 and 40 mL of essential oil of frankincense and between about 285 and 590 mL of safflower oil.

20. The method of claim 19, wherein the herbal composition further comprises between about 40 and 60 mL of an extract of cayenne.

21. The method of claim 20, wherein the extract of cayenne comprises at least 95 percent grain alcohol.

22. The method of claim 19, wherein the herbal composition further comprises cinnamon.

23. The method of claim 22, wherein the cinnamon comprises between about 20 and 30 mL of an essential oil of cinnamon bark.

24. The method of claim 19, wherein the herbal composition further comprises saffron.

25. The method of claim 19, wherein the saffron comprises between about 0.016 and 0.03 grams of powdered saffron.

26. The method of claim 15, wherein the area of edema comprises at least a part of a limb of the patient, and the massage strokes in the direction of venous blood flow are along said limb, in the direction of the heart.

27. The method of claim 15, wherein the area of edema comprises at least a part of the trunk of the patient, and the massage strokes in the direction of venous blood flow are in a widening spiral centered over the area of edema.

* * * * *